United States Patent [19]

Kiozpeoplou

[11] 4,383,987
[45] May 17, 1983

[54] FOAMING DENTIFRICE CONTAINING NONIONIC SURFACE ACTIVE AGENT

[75] Inventor: Diana Kiozpeoplou, Somerville, N.J.

[73] Assignee: Colgate/Palmolive Company, New York, N.Y.

[21] Appl. No.: 299,684

[22] Filed: Sep. 8, 1981

Related U.S. Application Data

[63] Continuation-in-part of Ser. No. 277,774, Jun. 26, 1981, abandoned.

[51] Int. Cl.³ ............................................. A61K 7/16
[52] U.S. Cl. ................................................... 424/49
[58] Field of Search ................................... 424/49–58

[56] References Cited

U.S. PATENT DOCUMENTS

| | | | |
|---|---|---|---|
| 2,677,700 | 5/1954 | Jackson et al. | 424/49 |
| 2,773,801 | 12/1956 | Fox | 424/57 |
| 2,991,229 | 7/1961 | Ivison | 424/49 |
| 3,976,765 | 8/1976 | Nachtigal | 424/54 |
| 4,011,309 | 3/1977 | Lutz | 424/49 |
| 4,206,198 | 6/1980 | Schmolka | 424/49 |
| 4,259,477 | 3/1981 | Kang | 424/49 |
| 4,323,552 | 4/1982 | Schmolka | 424/49 |
| 4,343,785 | 8/1982 | Schmolka | 424/54 |

FOREIGN PATENT DOCUMENTS

| | | |
|---|---|---|
| 2204670 | 8/1972 | Fed. Rep. of Germany . |
| 51-82739 | 7/1976 | Japan . |
| 53-34934 | 3/1978 | Japan . |
| 55-13251 | 1/1980 | Japan . |
| 1450881 | 3/1974 | United Kingdom . |
| 1425922 | 2/1976 | United Kingdom . |

OTHER PUBLICATIONS

Naganuma et al., Chem. Abstr. 93, #53809x (1980) of Jpn. Kokai Tokkyo Koho 80 13251, Jan 30, 1980.
Ozawa et al., Chem. Abstr. 89, #30797v (1978) of Japan Kokai 78 34934, Mar. 31, 1978.
Lawson et al., Chem. Abstr. 86, #78678x (1977) of Brit. 1450881, Sep. 29, 1976.
Morton, Chem. Abstr. 85, #25291p (1976) of Brit. 1425922 Feb. 25, 1976.
Ichikawa et al., Chem. Abstr. 85, #112767s (1976) of Japan Kokai 7682739, Jul. 20, 1976.
Clippingdale et al., Chem. Abstr. 77, #130502r (1972) of Ger. Offen. 2,204,670, Aug. 10, 1972.
Reng, Chem. Abstr. 86, #161019d (1977) of Parfuem. Kosmet. (1976) 57(11): 307-316, Foaming Agents for Products for Oral and Dental Hygiene.
McNeely and Kang, Industrial Gums Ed. R. L. Whistler Ch. XXI, 2nd Ed., N.Y. 1973, p. 473-497, "Xanthan".
Manufacturing Chemist, May 1960, pp. 206-208.

*Primary Examiner*—Shep K. Rose
*Attorney, Agent, or Firm*—Robert L. Stone; Murray M. Grill; Herbert S. Sylvester

[57] ABSTRACT

A foaming dentifrice containing a nonionic surface active agent. Foam is achieved through inclusion of about 1–10% by weight of a polyoxyethylene-polyoxypropylene block copolymer in combination with about 0.5–7% by weight of xanthan or xanthan about 0.5–7% by weight of and up to about 5% by weight of resinous poly (ethylene oxide) in a dentifrice comprising about 20–80% by weight of a liquid humectant vehicle.

8 Claims, No Drawings

FOAMING DENTIFRICE CONTAINING NONIONIC SURFACE ACTIVE AGENT

This application is a continuation-in-part of U.S. application Ser. No. 277,774 filed June 26, 1981, now abandoned.

This invention relates to a foaming dentifrice and in particular to a dentifrice in which nonionic surface active agent is employed.

Foam is a desirable characteristic of dentifrices since it spreads the dentifrice throughout the oral cavity during toothbrushing, thereby aiding in contacting the dentifrice with tooth surfaces and providing a characteristic mouth feel.

Foam, particularly full-bodied foam, is generally achieved by the use of an anionic surface active agent. Other surface active agents, and particularly non-ionic surface active agents, typically do not foam as well as the anionic surface active agents. Of the many anionic surface active agents only a few have been used commercially in dentifrices; the most commonly used one being sodium lauryl sulfate.

Anionic surface active agents may cause some mild side effects which some users may find somewhat undesirable. For example some users may experience temporary moderate irritation in the oral cavity, mild bitterness, sloughing of some oral mucosa or an unpleasant flavor reaction when drinking or eating citrus shortly after toothbrushing, when a dentifrice containing an anionic surface active agent is used.

Although it has been known that surface active properties could be provided to a dentifrice by a nonionic surface active agent, such an agent has not been commonly used since foaming is lost, unless supplemented with an anionic surface agent.

It is an advantage of this invention that a dentifrice containing a nonionic surface active agent and a particular binding agent is employed in which desirable stable full-bodied foaming is obtained.

It is a further advantage of this invention that the dentifrice employed is sweet without requiring the presence of a sweetening additive, and non-irritating, while also not being prone to cause users to experience sloughing of oral mucosa or have an adverse citrus flavor reaction after use of the dentifrice.

Further advantages of the invention will be apparent from consideration of the following specification.

In accordance with certain of its aspects, this invention relates to a dentifrice comprising about 20-80% by weight of a liquid humectant vehicle, about 0.5-7% by weight of xanthan gum, and about 1-10% by weight of a surface active agent consisting essentially of a nonionic polyoxyethylenepolyoxypropylene block copolymer. Preferably up to about 5% by weight of resinous poly (ethylene oxide) is also present.

The nonionic surface active agent employed in the instant invention is a block copolymer containing polyoxyethylene and polyoxypropylene. Such block copolymers are available from Wyandotte Chemicals Corporation under the trademark "Pluronic". They may be liquid, paste or solid and are generally chemically defined in terms of the molecular weight of the polyoxypropylene hydrophobic moiety and the percent of weight of the polyoxyethylene hydrophilic moiety. The following block copolymers are available from Wyandotte:

| PLURONIC NUMBER | PHYSICAL CHARACTER | % HYDRO-PHIL | MOL. WT. HYDROPHOBE |
|---|---|---|---|
| L 121 | LIQUID | 10 | 4000 |
| L 101 | LIQUID | 10 | 3250 |
| L 81 | LIQUID | 10 | 2250 |
| L 61 | LIQUID | 10 | 1750 |
| L 31 | LIQUID | 10 | 950 |
| L 122 | LIQUID | 20 | 4000 |
| L 92 | LIQUID | 20 | 2750 |
| L 72 | LIQUID | 20 | 2050 |
| L 52 | LIQUID | 20 | 1750 |
| L 42 | LIQUID | 20 | 1200 |
| P 123 | PASTE | 30 | 4000 |
| P 103 | PASTE | 30 | 3250 |
| L 63 | LIQUID | 30 | 1750 |
| L 43 | LIQUID | 30 | 1200 |
| P 104 | PASTE | 40 | 3250 |
| P 94 | PASTE | 40 | 2750 |
| P 84 | PASTE | 40 | 2250 |
| L 64 | LIQUID | 40 | 1750 |
| L 44 | LIQUID | 40 | 1200 |
| P 105 | PASTE | 50 | 3250 |
| P 85 | PASTE | 50 | 2250 |
| P 75 | PASTE | 50 | 2050 |
| P 65 | PASTE | 50 | 1750 |
| L 35 | LIQUID | 50 | 950 |
| F 127 | SOLID | 70 | 4000 |
| F 87 | SOLID | 70 | 2250 |
| F 77 | SOLID | 70 | 2050 |
| F 108 | SOLID | 80 | 3250 |
| F 98 | SOLID | 80 | 2750 |
| F 88 | SOLID | 80 | 2250 |
| F 68 | SOLID | 80 | 1750 |
| F 38 | SOLID | 80 | 950 |

The preferred nonionic block copolymers are solid (or flake) materials and the most preferred are Pluronic 108 (80% polyoxyethylene: 3250 molecular weight polyoxypropylene) and F 87 (70% polyoxyethylene: 2250 molecular weight polyoxypropylene). The nonionic surface active agent is employed in the dentifrice in amount of about 1-10% by weight, preferably about 2-5% and most preferably about 3%.

The binding or gelling agent system of xanthan or xanthan and resinous poly (ethylene oxide) co-operates with the nonionic surface active agent to provide stable full-bodied foaming and desirable mouth feel characteristics to the dentifrice. Xanthan gum, in the concentrations described, provides a stable full-bodied foam. The mouth feel characteristics can be modified as desired by the addition of resinous poly (ethylene oxide).

Resinous poly (ethylene oxide) has been disclosed as a dentifrice gelling or binding agent in U.S. Pat. No. 2,991,229 to Ivison. Its presence smooths the texture of the dentifrice.

The poly (ethylene oxides) employed in this invention are solid, colorless, water-soluble resins. They appear to form homogeneous systems in water in all proportions, although the relatively higher molecular weight ethylene oxide polymers merely swell on the addition of small amounts of water. On the addition of greater amounts of water, the polymers pass into solution. The water solutions are viscous, the viscosity increasing both with the concentration of the polymer in the solution and the reduced viscosity of the polymer. The ethylene oxide polymers employed in this invention show little change in melting point with increased reduced viscosity (an indication of increased molecular weight) and the melting point, as measured by change in stiffness with temperature, was found to be about 65°±2° C. throughout the range of reduced viscosities of from about 1.0 to about 10, and greater. These polymers, upon X-ray examination, disclose a crystalline structure similar to that exhibited by polyethylene. The crystallization temperature, as determined from measuring the break in the cooling curve, is about 55° C.

To facilitate the understanding of the instant invention, various terms will be defined. At the outset it should be noted that the word "poly (ethylene oxide)" as used throughout the specification and claims refers to ethylene oxide polymers which have a reduced viscosity in acetonitrile of at least 0.5 and upwards to 75, and higher.

Unless otherwise stated, by the term "reduced viscosity", as used herein, is meant a value obtained by dividing the specific viscosity by the concentration of the ethylene oxide polymer in the solution, the concentration being measured in grams of polymer per 100 milliliters of solvent at a given temperature, and is regarded as a measure of molecular weight. The specific viscosity is obtained by dividing the difference between the viscosity of the solution and the viscosity of the solvent by the viscosity of the solvent. The reduced viscosities herein referred to are measured at a concentration of 0.2 gram of poly (ethylene oxide) in 100 milliliters of acetonitrile at 30° C. (unless stated otherwise).

Granular poly (ethylene oxide) results from the suspension polymerization of an agitated reaction mixture comprising ethylene oxide in contact with a polymerization catalyst therefor and in the presence of an inert organic diluent, e.g., heptane, in which ethylene oxide is soluble and the resulting poly (ethylene oxide) is insoluble). Granular poly (ethylene oxide) thus produced is obtained in a finely-divided solid particle state and resembles finely-divided sand in particle size. Unlike the granular poly (ethylene oxide) resulting from the suspension polymerization process, the bulk and solution polymerization processes yield a polymer which is substantially a homogeneous mass either conforming to the shape of the reaction vessel or, after driving off the organic medium, for example, by mechanical extrusion, e.g., Marshall Mill (under vacuum and at slightly elevated temperatures), resembles layers or sheets. This polymer subsequently can be reduced in particle size, for example, by dicing or the like.

The term "granular" refers to the particle size of the ethylene oxide polymers prepared by suspension polymerization. A granular product is one which is a free-flowing state and comprises particles averaging less than 5 mesh in size (U.S. Standard Size Sieve). When present, the poly (ethylene oxide) comprises up to about 5% by weight of the dentifrice, perferably about 0.1-1.5%.

Xanthan has been disclosed as a dentifrice gelling or binding agent in U.S. Pat. application Ser. No. 293,424, filed Aug. 17, 1981, based on British Application No. 80 26943 filed Aug. 19, 1980 by Colgate Palmolive Company.

Xanthan gum is a fermentation product prepared by action of the bacteria of the genus Xanthomonas upon carbohydrates. Four species of Xanthomonas, viz. X. campetris. X. phaseoli, X. malvocearum, and X. carotae are reported in the literature to be the most efficient gum producers. Although the exact chemical structure is not determined, it is generally accepted to be a heteropolysaccharide with a molecular weight of several million. It contains D-glucose, D-mannose, and D-glucoronic acid in molar ratio of 2.8:3:2.0. The molecule contains 4.7% acetyl and about 3% pyruvate. The proposed chemical structure configuration can be found in McNeely and Kang, Industrial Gums, ed. R. L. Whistler, CH XXI 2nd Edition, New York, 1973. The procedure for growing, isolating and purifying the xanthan gum is found in Manufacturing Chemist, May 1960, pages 206-208 (including mention at page 208 of potential use of gums therein described for formulating toothpastes).

Use of special grades of xanthan gum, such as described in U.S. Pat. No. 4,263,399 are within the scope of this invention. A grade described in U.S. Pat. No. 4,263,399 is a xanthan gum in which up to about 1.6% of the carboxyl groups are bound to calcium and the remaining carboxyl groups are bound to sodium, potassium, a mixture of sodium and potassium or other non-calcium cations.

The xanthan gelling agent is present in amount of about 0.5-7% by weight of the dentifrice, preferably about 1.5-3%.

Since the nonionic surface active agent is used in the present invention, the moderate bitterness generally contributed by an anionic surface active agent is not experienced by users. Accordingly, sweetening agents which are often added to dentifrices at least in part to overcome the bitterness, are less needed in the dentifrice of this invention in comparison with prior art practice. Indeed, sufficient satisfactory sweetness can be readily provided by the low sweetening character of many humectants which are commonly employed in dentifrice compositions. Such humectants are comprised in the liquid phase of the dentifrice, typically together with water. Typical humectants include sorbitol (as 70% aqueous solution), glycerine, maltitol, xylitol and polyethylene glycol 400. The liquid phase comprises about 20-80% by weight of the dentifrice, preferably about 30-60%, with water (if present) typically being in amount up to about 60% and humectant typically being about 20-60%. It is noted that maltitol is disclosed as a dentifrice ingredient in Japanese Patent Publications 73/10241 and 65/15120.

The liquid vehicle and gelling agent and other components of the dentifrice are proportioned to form a cream or gel mass of desired consistency which is extrudible from an aerosol or pump container or a collapsible tube (for example aluminum, lead or plastic).

The dentifrice typically contains a dentally acceptable polishing agent which is generally substantially water-insoluble of the type commonly employed in dental creams. Representative polishing agents include, for example, dicalcium phosphate, tricalcium phosphate, insoluble sodium metaphosphate, aluminum hydroxide including hydrated alumina, calcined alumina, colloidal silica, magnesium carbonate, calcium carbonate, calcium pryophosphate, bentonite, etc. including suitable mixtures thereof. When employed, it is preferred to use the water insoluble phosphate salts as the polishing agent and more particularly insoluble sodium metaphosphate and/or a calcium phosphate such as dicalcium phosphate dihydrate in dental creams. When visually clear gels or opacified gels are employed, a polishing agent of colloidal silica, such as those sold under the trademark Syloid as Syloid 72 and Syloid 74 or under the trademark Santocel as Santocel 100 and synthetic alkali metal aluminosilicate complexes or silica containing combined alumina may be particularly useful. When employed, the polishing agent content is generally in amounts from about 15 to 75% by weight in a dental cream and about 5 to 50% by weight in a clear or opacified gel.

The compositions of the present invention, may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2·KF$), potassium fluorozirconate, sodium hexafluorostannate, stannous chlorofluoride, and sodium monofluorophosphate. These materials, which dissociate or release fluorine-containing ions, suitably may be present in an effective but non-toxic amount, usually within the range of about 0.1 to 1% by weight, based on the water soluble fluorine content thereof. Sodium fluoride, stannous fluoride and sodium monofluorophosphate are particularly preferred, as well as mixtures thereof.

Antibacterial agents may also be employed in the oral preparations of the instant invention to provide a total content of such agents of up to about 5% by weight. Typical antibacterial agents include $N^1$-(4-chlorobenzyl)-$N^5$-(2,4-dichlorobenzyl) biguanide;
p-chlorophenyl biguanide;
4-chlorobenzyhydryl biguanide;
4-chlorobenzydrylguanylurea;
N-3-lauroxypropyl-$N^5$-p-chlorobenzylbiguanide;
1-(lauryldimethylammonium)-8-(p-chlorobenzyl-dimethylammonium) octane dichloride;
5,6-dichloro-2-guanidinobenzimidazole;
$N^1$-p-chlorophenyl-$N^5$-laurylbiguanide;
1,6-di-p-chlorophenyl biguanidohexane;
1,6-bis(2-ethylhexyl biguanido) hexane;
5-amino-1,3-bis(2-ethylhexyl)-5-methylhexahydropyrimidine;

and their non-toxic acid addition salts.

Synthetic finely divided pyrogenic silica such as those sold under the trademarks Cab-O-Sil M-5, Syloid 244, Syloid 266 and Aerosil D-200 may also be employed in amounts of about 1–5% by weight to promote thickening or gelling and to improve clarity of the dentifrice.

The taste of the new compositions may be modified by employing suitable flavoring or sweetening materials. Examples of suitable flavoring constituents include the flavoring oils, e.g. oils or spearmint, peppermint, wintergreen, sassafras, clove, sage, eucalyptus, marjoram, cinnamon, lemon and orange as well as methylsalicylate. Suitable sweetening agents include sucrose, lactose, maltose, sorbitol, sodium cyclamate, perillartine and saccharine. Suitable, flavor agent may comprise from about 0.01 to 5% or more of the composition of the instant invention. As mentioned above, sweetening agents are less necessary in the dentifrice of the present invention than in dentifrices of the prior art which have contained anionic surface active agent since slight bitterness from the anionic surface active agent need not be masked. Nevertheless, if desired, for instance, if the flavor has a pronounced menthol note, about 0.05–1% of sweetening agent can be used to provide taste modifications as desired.

Various other materials may be incorporated in the dentifrice formulations of this invention. Examples thereof are coloring or whitening agents or dyestuffs, preservatives, silicones, chlorophyll compounds, ammoniated materials such as urea, diamoniumphosphate and mixtures thereof, and other constituents. The adjuvants are incorporated in the instant compositions in amounts which do not substantially adversely effect the properties and characteristics are desired and selected and used in proper amount depending upon the particular type of preparation involved.

The following specific example is further illustrative of the nature of the present invention but it is understood that the invention is not limited thereto. Dentifrice formulations are prepared in the usual manner, except as indicated, and all amounts and proportions are by weight except as otherwise indicated.

EXAMPLES

The following opacified gel dentifrices are prepared:

| | EXAMPLE | |
|---|---|---|
| | 1 Control | 2 |
| Glycerine | 10.0 | 10.0 |
| Maltitol | 15.0 | 15.0 |
| Sodium aluminosilicate (silica with combined alumina) | 18.0 | 18.0 |
| Pluronic 108 block copolymer | — | 3.0 |
| Sodium lauryl sulfate | 1.0 | — |
| Xanthan | 2.0 | 2.0 |
| Polyox WSR 301 | 0.2 | 0.2 |
| Sodium monofluorophosphate | 0.76 | 0.76 |
| Titanium dioxide | 0.4 | 0.4 |
| Low menthol flavor | 0.5 | 0.5 |
| Sodium saccharin | 0.2 | — |
| Color solution (1%) | 0.05 | 0.05 |
| Water | Q.S. to 100 | Q.S. to 100 |

The dentifrice of Example 1 with sodium lauryl sulfate has desirable foam character but a bitter taste. The dentifrice of Example 2 also has very good stable full-bodied foam character even though no anionic surface active agent is employed. The foam remains throughout the oral cavity, with desirable mouth feel, when the dentifrice is brushed onto the teeth. Moreover, it has no bitter note even though no sweetener is added. If the flavor were to have a high menthol note, it would be readily masked with 0.1 part of sodium saccharin. The dentifrices have fine smooth texture.

Similar desirable results are obtained when xanthan of Example 2 is replaced with the low-calcium xanthan of Example 1 of U.S. Pat. No. 4,263,399.

Similar foam and feel is attained when other block copolymers of polyoxyethylene and polyoxypropylene replace Pluronic F-108, particularly Pluronic F 87.

Polyox WSR-301 is available from Union Carbide Corp. as granules of water soluble poly (ethylene oxide) resin having a molecular weight of about 4,000,000 and a Brookfield viscosity of 1650–3850 cps. (25° C., spindle 1, speed 2 rpm) when in water at 1% by weight. Likewise, similar foam and feel is attained when other water-soluble poly (ethylene oxide) resins available from Union Carbide Corp. as Polyox WSR-N-10WSR-N-80, WSR-N-750, WSR-N-3000, WSR-205 and WSR-1105 replace Polyox WSR-301, in different concentrations.

The silica with combined alumina employed in the above dentifrices and in those of Examples 3 to 11 below is obtained from the J. M. Huber, Corp. of Havre de Grace, Maryland, as Zeo 49.

The following clear gel (3 and 4) and opacified gel (5 and 6) dentifrices are prepared:

| | EXAMPLES | | | |
|---|---|---|---|---|
| | 3 | 4 | 5 | 6 |
| Glycerine | 10.0 | — | 10.0 | — |
| Sorbitol (70%) | 16.0 | — | 15.0 | — |
| Maltitol | 16.0 | 35.0 | 15.0 | 30.0 |
| Sodium aluminosilicate (silica with combined alumina) | 22.0 | 18.0 | 18.0 | 18.0 |
| Pluronic F-108 | 3.0 | 3.0 | 5.0 | — |
| Pluronic F-87 | — | — | — | 3.0 |
| Xanthan | 1.5 | 2.0 | 2.0 | 2.0 |
| Polyox WSR-301 | 0.2 | 0.2 | 0.2 | 0.2 |
| Sodium monofluorophosphate | 0.76 | 0.76 | 0.76 | 0.76 |
| Titanium dioxide | — | — | 0.4 | 0.4 |
| Low menthol flavor | 0.5 | 0.5 | 0.5 | 0.5 |
| Color solution (1%) | 0.05 | 0.05 | 0.05 | 0.05 |
| Water | Q.S. to 100 | Q.S. to 100 | Q.S. to 100 | Q.S. to 100 |

The dentifrices of Examples 3 and 4 are clear and those of Examples 5 and 6 are opacified,. They have smooth texture. All four have very good stable full-bodied foam, with that of the dentifrice of Example 5 being more full then with the dentifrices of Examples 3 and 4. A higher amount of foam occurs with the dentifrices of Examples 6. All foams provide desirable mouth feel throughout the entire oral cavity during tooth brushing. There are no bitter notes.

The following dentifrices are prepared:

| | EXAMPLES | | | | |
|---|---|---|---|---|---|
| | 7 | 8 | 9 | 10 | 11 |
| Maltitol | 30.0 | 30.0 | 30.0 | 30.0 | 30.0 |
| Sodium aluminosilicate (silica with combined alumina) | 12.0 | 12.0 | 12.0 | 18.0 | 15.0 |
| Calcined alumina | 5.0 | 5.0 | 5.0 | 5.0 | 2.0 |
| Pluronic F-108 | 3.0 | 3.0 | 3.0 | 3.0 | 3.0 |
| Xanthan | 2.0 | 2.0 | 2.0 | 1.7 | 2.0 |
| Polyox WSR-301 | 0.2 | — | — | 0.2 | 0.2 |
| WSR-1105 | — | 0.2 | — | — | — |
| WSR-N-750 | — | — | 1.0 | — | — |
| Sodium monofluorophosphate | 0.76 | 0.76 | 0.76 | 0.76 | 0.76 |
| Titanium dioxide | 0.4 | 0.4 | 0.4 | 0.4 | 0.4 |
| Low menthol flavor | 0.5 | 0.5 | 0.5 | 0.5 | 0.5 |
| Water | Q.S. to 100 | Q.S. to 100 | Q.S. to 100 | Q.S. to 100 | Q.S. to 100 |

The dentifrices of Examples 7-11 provide high cleaning effectiveness and have good, stable, full-bodies foam. They have smooth texture, with the dentifrices of Examples 7,10 and 11 containing Polyvox WSR-301 having the best texture. All foam to provide desirable mouth feel throughout the entire oral cavity during toothbrushing. There are no bitter notes.

The following dentifrices are prepared:

| | EXAMPLES | | | |
|---|---|---|---|---|
| | 12 | 13 | 14 | 15 |
| Glycerine | 10.0 | 10.0 | 10.0 | 10.0 |
| Sorbitol (70%) | 15.0 | 15.0 | 15.0 | 15.0 |
| Maltitol | 15.0 | 15.0 | 15.0 | 15.0 |
| Dicalcium phosphate dihydrate | 30.0 | 30.0 | 15.0 | 15.0 |
| Anhydrous dicalcium phosphate | — | — | 10.0 | — |
| Calcined alumina | — | — | — | 10.0 |
| Pluronic F-108 | 3.0 | 3.0 | 3.0 | 3.0 |
| Xanthan | 2.0 | 2.0 | 2.0 | 2.0 |
| Polyox WSR-301 | — | 0.2 | 0.2 | 0.2 |
| Sodium monofluorophosphate | 0.76 | 0.76 | 0.76 | 0.76 |
| Titanium dioxide | 0.4 | 0.4 | 0.4 | 0.4 |
| Low menthol flavor | 0.5 | 0.5 | 0.5 | 0.5 |
| Water | Q.S. to 100 | Q.S. to 100 | Q.S. to 100 | Q.S. to 100 |

The dentifrices of Examples 12-15 provide good, stable full-bodied foam. Those of Examples 13-15 (which contain the Polyox material) have particularly fine, smooth texture. The foam from all gives desirable mouth feel throughout the oral cavity during toothbrushing. Even though no sweetener is used, the dentifrices are quite sweet in taste.

This invention has been described with respect to the above illustrative dentifrices and it will be understood that modifications and variations thereof obvious to those skilled in the art to be included within the spirit and purview of this application and the scope of the appended claims.

I claim:

1. A foaming dentifrice having stable, full-bodied foam character comprising about 20-80% by weight of a liquid humectant vehicle, about 0.5-7% by weight of xanthan gum effective to provide said stable full-bodied foam and about 1-10% of a surface active agent consisting essentially of a nonionic polyoxyethylene-polyoxypropylene block copolymer.

2. The dentifrice claimed in claim 1 wherein said block copolymer is a solid material.

3. The dentifrice claimed in claim 2 wherein said solid block copolymer contains about 80% by weight polyoxyethylene and the molecular weight of said polyoxypropylene is about 3250 or about 70% by weight polypropylene and the molecular weight of said polyoxypropylene is about 2250.

4. The dentifrice claimed in claim 1 wherein resinous poly (ethylene oxide) is present in amount of about 0.1-5% by weight.

5. The dentifrice claimed in claim 4 wherein said block copolymer is a solid material.

6. The dentifrices claimed in claim 5 wherein said solid block copolymer contains about 80% by weight polyoxyethylene and the molecular weight of said polyoxypropylene is about 3250 or about 70% polyoxyethylene and the molecular weight of said polyoxypropylene is about 2250.

7. The dentifrice claimed in claim 4 wherein about 1.5-3% by weight xanthan and 0.1-1.5% by weight of said resinous poly (ethylene oxide) is present.

8. The dentifrice claimed in claim 1 wherein said liquid humectant vehicle comprises glycerine, sorbitol, maltitol and mixtures thereof.

* * * * *